(12) United States Patent
Laughlin et al.

(10) Patent No.: US 11,406,815 B2
(45) Date of Patent: Aug. 9, 2022

(54) ELECTRICAL STIMULATION SYSTEM (71) Applicant: The Boeing Company, Chicago, IL (US)

(72) Inventors: Brian Dale Laughlin, Wichita, KS (US); Dane Brian Laughlin, Wichita, KS (US); Madison Lauryn Laughlin, Wichita, KS (US)

(73) Assignee: The Boeing Company, Chicago, IL (US)

( * ) Notice: Subject to any disclaimer, the term of this patent is extended or adjusted under 35 U.S.C. 154(b) by 140 days.

(21) Appl. No.: 16/415,788

(22) Filed: May 17, 2019

(65) Prior Publication Data
US 2020/0360684 A1 Nov. 19, 2020

(51) Int. Cl.
*A61N 1/05* (2006.01)
*A61N 1/36* (2006.01)
*A61N 1/20* (2006.01)

(52) U.S. Cl.
CPC ....... *A61N 1/0534* (2013.01); *A61N 1/36062* (2017.08); *A61N 1/36182* (2013.01); *A61N 1/20* (2013.01); *A61N 1/36082* (2013.01)

(58) Field of Classification Search
CPC .. A61N 1/0534; A61N 1/0536; A61N 1/0568; A61N 1/36062; A61N 1/0448; A61N 1/0529; A61N 1/3606
See application file for complete search history.

(56) References Cited

U.S. PATENT DOCUMENTS

| | | | |
|---|---|---|---|
| 4,406,658 A | 9/1983 | Lattin et al. | |
| 8,649,873 B2 | 2/2014 | Moffitt et al. | |
| 2005/0096720 A1* | 5/2005 | Sharma | A61B 5/283 607/122 |
| 2007/0100398 A1* | 5/2007 | Sloan | A61N 1/36082 607/62 |
| 2009/0054955 A1 | 2/2009 | Kopell et al. | |
| 2013/0197373 A1 | 8/2013 | Sharma et al. | |
| 2014/0074182 A1* | 3/2014 | Wolf, II | A61N 1/3616 607/46 |
| 2018/0103848 A1 | 4/2018 | Kinser et al. | |
| 2020/0398058 A1* | 12/2020 | Pivonka | G16H 40/67 |

OTHER PUBLICATIONS

Extended European Search Report, dated Oct. 22, 2020, regarding Application No. 20171103.3, 8 pages.
Tanimola, "Distributed Fibre Optic Sensors for Pipeline Protection," Journal of Natural Gas Science and Engineering, vol. 1, Issue 4, Nov. 2009, 20 pages.

* cited by examiner

*Primary Examiner* — Lynsey C Eiseman
*Assistant Examiner* — Jessica L Mullins
(74) *Attorney, Agent, or Firm* — Yee & Associates, P.C.

(57) ABSTRACT

A method, apparatus, and system for delivering an electrical current. Optical signals are sent through a group of optical fibers in a medium. Response optical signals occurring in response to the optical signals sent through the group of optical fibers are detected when the group of optical fibers is located in the medium. A group of parameters for the medium is determined using the response optical signals. A group of electrical currents is sent through a group of electrodes based on the group of parameters, wherein the group of electrodes emit the group of electrical currents.

27 Claims, 8 Drawing Sheets

ELECTRICAL STIMULATION SYSTEM

BACKGROUND INFORMATION

1. Field

The present disclosure relates generally to biomedical systems and in particular, to a method, apparatus, and system for delivering an electrical current into a tissue.

2. Background

As people age, their brains become less efficient at managing the electro-chemical nervous signals it generates, sometimes leading to decreased motor function capabilities. In some extreme cases, such as Essential Tremors and Parkinson's disease, the brain effectively "short circuits" resulting in chronic, uncontrollable, spasmodic musculoskeletal movements. These conditions increasingly incapacitate the patient over time, if left untreated.

These disorders are often treated using medications. The medications do not always work as desired. Other types of treatment are also present. One type of treatment is deep brain stimulation (DBS), which can provide relief and restore a great degree of motor function.

Electrical brain stimulation can be used to treat these conditions. For example, deep brain stimulation uses a medical device called a neurostimulator, which sends electrical impulses through implanted electrodes to specific targets in the brain for the treatment of movement and neuropsychiatric disorders. These electrodes transmit low-level electrical pulses that effectively buffer and normalize neurological misfiring in the brain.

Deep brain stimulation in select brain regions has provided therapeutic benefits for otherwise treatment-resistant disorders. Deep brain stimulation directly changes brain activity in a controlled manner.

Although deep brain stimulation may be effective in treating these disorders, the underlying principles and mechanisms are still not clear. The pulse generator may be programmed by sending electrical signals through electrodes in the brain that have a selected pulse width, voltage amplitude, and frequency. Adjustments to these parameters may be made to obtain desired results in a patient, such as a reduction in tremors.

Currently, adjustments can be made by observing the patient to see whether changes such as fewer spasmodic musculoskeletal movements or increased motor skills are present. These visual observations are useful but granularity in the level of feedback for making adjustments may be coarser than desired.

Therefore, it would be desirable to have a method and apparatus that take into account at least some of the issues discussed above, as well as other possible issues. For example, it would be desirable to have a method and apparatus that overcome a technical problem with obtaining a finer level of feedback than provided by visual observations of a patient.

SUMMARY

An example of the present disclosure provides an electrical stimulation system comprising a group of electrodes; a group of optical fibers; and a controller that controls operation of the group of electrodes and the group of optical fibers. The controller sends optical signals through the group of optical fibers; detects response optical signals occurring in response to the optical signals sent through the group of optical fibers when the group of optical fibers is located in a medium. The controller determines a group of parameters for the medium using the response optical signals and sends a group of electrical currents through the group of electrodes based on the group of parameters, wherein the group of electrodes emit the group of electrical currents into the medium when the group of electrodes is located in the medium.

Another example of the present disclosure provides an electrical stimulation system comprising electrodes, optical fibers, and a controller. The electrodes have tubular shapes with exterior surfaces and interior surfaces in cavities in the electrodes. The optical fibers are configured to be placed into an interior of a system. The optical fibers are located on at least one of the exterior surfaces or the interior surfaces. The controller sends optical signals through the optical fibers detects response optical signals occurring in response to the optical signals sent through optical fibers when the optical fibers is located in a medium. The controller determines a group of parameters for the medium using the response optical signals and sends a group of electrical currents through the electrodes based on the group of parameters. The electrodes emit the group of electrical currents into the medium when the electrodes are located in the medium.

Yet another example of the present disclosure provides a method for delivering an electrical current. Optical signals are sent through a group of optical fibers in a medium. Response optical signals occurring in response to the optical signals sent through the group of optical fibers are detected when the group of optical fibers is located in the medium. A group of parameters for the medium is determined using the response optical signals. A group of electrical currents is sent through a group of electrodes based on the group of parameters, wherein the group of electrodes emit the group of electrical currents.

The features and functions can be achieved independently in various examples of the present disclosure or may be combined in yet other examples in which further details can be seen with reference to the following description and drawings.

BRIEF DESCRIPTION OF THE DRAWINGS

The novel features believed characteristic of the illustrative examples are set forth in the appended claims. The illustrative examples, however, as well as a preferred mode of use, further objectives and features thereof, will best be understood by reference to the following detailed description of an illustrative example of the present disclosure when read in conjunction with the accompanying drawings, wherein:

DETAILED DESCRIPTION

The illustrative examples recognize and take into account one or more different considerations. The illustrative examples recognize and take into account that it may be desirable to have other feedback in addition to visual observations to determine what changes should be made in the electrical stimulation performed using a brain stimulation system. For example, the illustrative examples recognize and take into account that these visual observations are unable to determine whether the electrical current from electrical stimulation is reaching a desired volume of neurons in the brain that may benefit from the electrical stimulation. For example, the illustrative examples recognize and take into account that detecting the electrical activity of neurons can be used to identify target neurons that may benefit from electrical stimulation through an electrical current.

Thus, the illustrative examples provide a method, apparatus, and system for delivering electrical current in a medium. In one illustrative example, an electrical stimulation system comprises a group of electrodes, a group of optical fibers, and a controller. The controller is connected to the group of electrodes and the group of optical fibers. The controller sends optical signals through the group of optical fibers and detects response optical signals occurring in response to the optical signals sent through the group of optical fibers when the group of optical fibers is located in a medium. The controller determines a group of parameters for the medium using the response optical signals and sends a group of electrical currents through the group of electrodes based on the group of parameters, wherein the group of electrodes emit the group of electrical currents into the medium when located in the medium.

As used herein, the phrase "a group of," when used with reference with items, means one or more items. For example, a "group of electrodes" is one or more electrodes.

Figure 1:
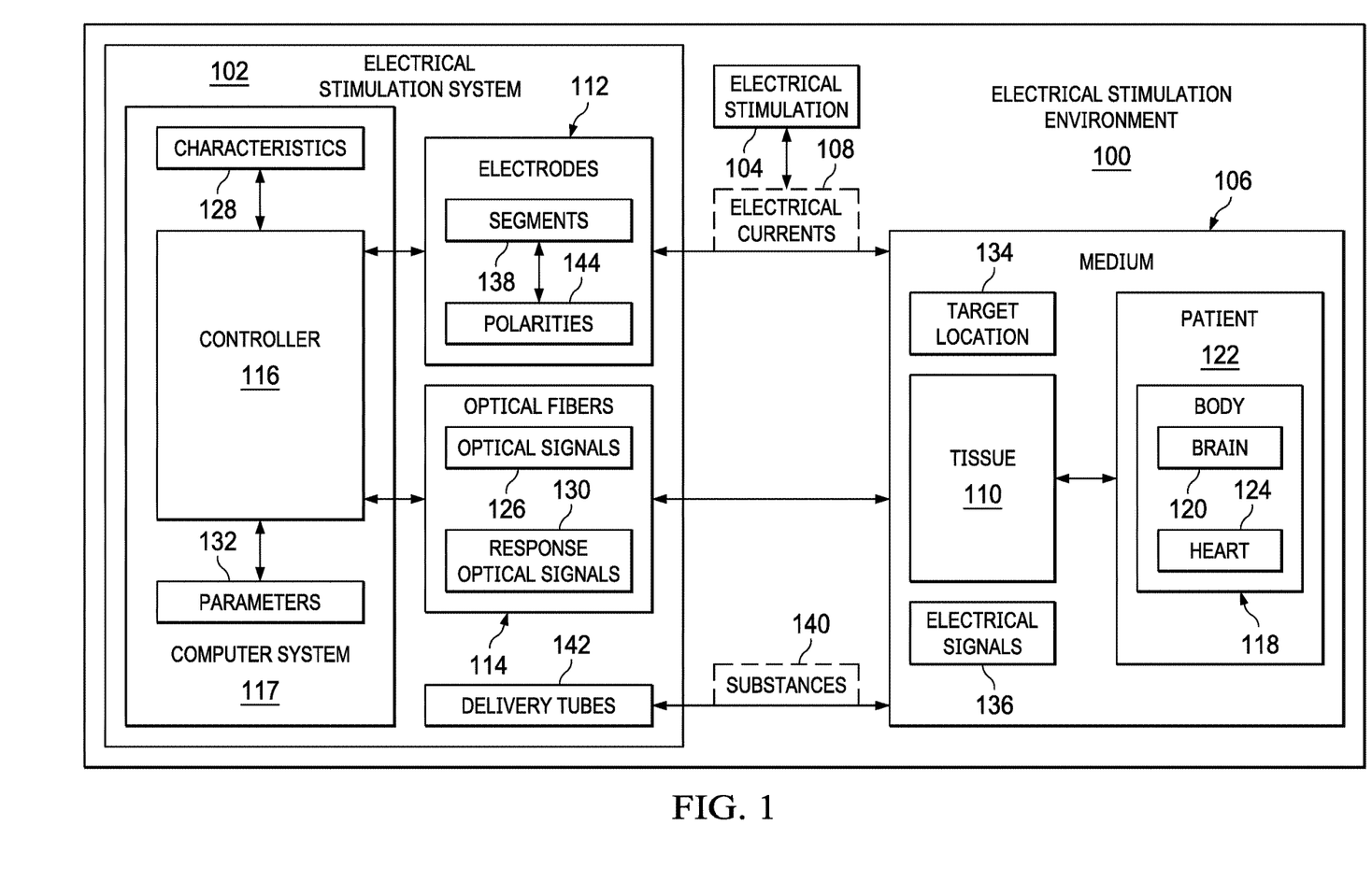
FIG. 1 is an illustration of an electrical stimulation environment in accordance with an illustrative example.

With reference now to the figures in particular with reference to FIG. 1, an illustration of an electrical stimulation environment is depicted in accordance with an illustrative example. In electrical stimulation environment 100, electrical stimulation system 102 can apply electrical stimulation 104 to medium 106. As depicted, electrical stimulation 104 can take the form of electrical currents 108.

In this illustrative example, medium 106 is a body or a structure in a living organism such as a person or animal. In another example, medium 106 can be the living organism. Medium 106 can be, for example, tissue 110. Tissue 110 is a cellular organizational level between cells and an organ. Tissue 110 can comprise similar cells and their extracellular matrix. An example of tissue 110 can be connective tissue, muscular tissue, nervous tissue, or epithelial tissue. Medium 106 can also be organs or structures in organs in addition to tissue 110.

As depicted, electrical stimulation system 102 comprises a number of different components. In this illustrative example, electrical stimulation system 102 includes a group of electrodes 112, a group of optical fibers 114, and controller 116.

In this illustrative example, the group of electrodes 112 and the group of optical fibers 114 are located in medium 106 during operation of electrical stimulation system 102. As depicted, the group of electrodes 112 and the group of optical fibers 114 can be temporarily implanted or implanted on a permanent basis.

The group of electrodes 112 is a group of conductors through which a group of electrical currents 108 can flow into medium 106. The group of optical fibers 114 is a group of flexible transparent fibers though which optical signals 126 can be transmitted. The group of optical fibers 114 form a sensor system in electrical stimulation system 102.

In the illustrative examples, the group of electrodes 112 and the group of optical fibers 114 can be placed with tissue 110 such as nervous tissue in brain 120 of body 118 such as for patient 122. When the group of electrodes 112 are located in brain 120, the group of electrical currents 108 can be emitted to perform at least one of cranial electrotherapy stimulation, deep brain stimulation, transcranial direct current stimulation, electroconvulsive therapy, low field magnetic stimulation, functional electrical stimulation, vagus nerve stimulation, deep transcranial magnetic stimulation, or other types of stimulation.

The group of electrical currents 108 through medium 106 to cause a change in tissue 110 such as nervous tissue in brain 120. The group of electrical currents 108 can cause a number of effects including at least one of depolarization blockade, synaptic inhibition, desynchronization, antidromic activation, or other effects. Depolarization blockade occurs when electrical currents block the neuronal output at or near the electrode site. Synaptic inhibition causes an indirect regulation of the neuronal output by activating axon terminals with synaptic connections to neurons near the stimulating electrode. Desynchronization involves depolarizing of abnormal oscillatory activity of neurons. Antidromic activation involves either activating or blockading distant neurons or blockading slow axons.

In another illustrative example, the group of electrodes 112 and the group of optical fibers 114 can be placed near or on tissue 110 such as a cardiac muscle for heart 124 in body 118 of patient 122.

When the group of electrodes 112 are located in heart 124, in contact with heart 124, or in proximity, the group of electrical currents 108 can reach heart 124. The group of electrical currents 108 can be emitted to perform at least one of a heart rate control, a cardioversion, a defibrillation, or other suitable operations on heart 124.

As used herein, the phrase "at least one of," when used with a list of items, means different combinations of one or more of the listed items can be used, and only one of each item in the list may be needed. In other words, "at least one of" means any combination of items and number of items may be used from the list, but not all of the items in the list are required. The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

As used herein, the phrase, a "number of" when used with reference to items means one or more items. For example, a number of effects is one or more effects.

A number of characteristics 128 of the group of electrical currents 108 can be selected. For example, number of characteristics 128 comprises at least one of an amplitude, a voltage, a frequency, an electrode current flow, a direct current flow, an alternating current flow, a pattern in current flow, or other characteristic for the group of electrical currents 108.

Each current in the group of electrical currents 108 can have a different value for a particular characteristic or the same value as compared to another current in the group of electrical currents 108. In this illustrative example, the pattern of current flow can describe a pattern for at least one of a pulse length, a width, an amplitude, or other characteristic for an electrical current.

Current flow is between conducting elements in the group of electrodes 112. For example, the conducting elements can be segments 138 that form the group of electrodes 112. Each electrode can have a plurality of segments 138. The group of electrical currents 108 can flow from at least one of segments 138.

For example, electrode current flow can be from one electrode to another electrode, from one segment in an electrode to a second segment in the electrode or another electrode, from one electrode to many electrodes, from one electrode to many segments, from one segment to many electrodes, or from one segment to many segments.

For example, the group of electrical currents 108 have characteristics 128 such that the group of electrical currents 108 emitted from the group of electrodes 112 flow between the group of electrodes 112 with a desired shape. This flow between the group of electrodes 112 can be between segments 138 in the group of electrodes 112. The desired shape can be a sphere, a cylinder, a frustrum, or some other three-dimensional shape.

In this illustrative example, polarities 144 for segments 138 can be set independently. This feature can be used in setting a desired shape of the group of electrical currents 108. In other words, a polarity of one segment to can be set to positive while the polarity of another segment can be set to negative. In this manner, multiple types of current flow can be selected between segments 138 in an electrode in the group of electrodes 112 or between segments 138 in other electrodes in the group of electrodes 112. Thus, this ability to select the polarity for segments 138 can be used to select a shape for current flow of electrical currents 108 between at least one of electrodes 112 or segments 138. When all of segments 138 in an electrode have the same polarity, the current flow is characterized as being to or from an electrode rather than from a particular segment.

Thus, the current flow for the group of electrical currents 108 can be controlled by controlling the polarity of segments 138. In this illustrative example, the polarities of segments 138 can be reversible for segments on an electrode and can be interchanged from segment to segment for numerous configurations such that a current loop pathway can be shaped as it traverses medium 106 such as brain structures. The polarities 144 segments 138 can switch on some predetermined trigger-based frequency such as time, threshold, external event, or some other factor. This feature enables the polarity switching to cause changes from the current flow. Based on the detected changes, the current flow can be altered, as well as pulsing, ramp up, frequency, amplitude, or other characteristics of the electrical currents.

With this ability to control the shape of the flow of the group of electrical currents 108, the current flow can be directed more specifically to an intended target while reducing exposure of other portions of medium 106 to the group of electrical currents 108.

For example, when medium 106 is tissue 110 in brain 120, the current flow for the group of electrical currents 108 can be shaped to more precisely target specific brain structures in brain 120. With this ability to select specific structures, the electrical stimulation system 102 can be operated to precisely deliver the group of electrical currents 108 to treat conditions such as for example, Essential Tremors and Parkinson's spasms in a manner that reduces the amount of power delivered into the brain tissue. In the illustrative example, electrical stimulation system 102 includes the ability to select specific brain structures can reduce affecting areas for tissue 110 that are not intended targets of the electrical current. Further, electrical stimulation system 102 reduces the amount of current needed to treat these conditions in addition to or precisely target tissue 110 to treat these and other conditions.

One or more illustrative examples can direct the electrical currents precisely to target location 130 for tissue 110. For example, the current may be directed from one electrode to another electrode to pass through target location 130 rather than generally emitting current through tissue 110 without any particular direction or shape. Additionally, this type of shape and can also reduce desensitization and prolong treatment effectiveness.

In this illustrative example, optical signals 126 are sent through the group of optical fibers 114. Response optical signals 130 can be detected in response to optical signals 126 sent through the group of optical fibers 114. In this example, response optical signals 130 can be used to determine a group of parameters 132 for medium 106. These parameters can be determined by comparing response optical signals 130 to optical signals 126. In this illustrative example, the group of parameters 132 can be selected from at least one of a heart rate, a temperature, a blood pressure, a blood oxygen level, or other parameters about medium 106 when medium of 106 is tissue 110.

As depicted controller 116 in computer system 117 controls the group of electrodes 112 and the group of optical fibers 114. Controller 116 operates to send optical signals 126 through the group of optical fibers 114 and detect response optical signals 130 occurring in response to optical signals 126 sent through the group of optical fibers 114 when the group of optical fibers 114 is located in medium 106. Further, controller 116 can determine the group of parameters 132 for medium 106 using response optical signals 130. Controller 116 can send a group of electrical currents 108 through the group of electrodes 112 based on the group of parameters 132. The group of electrodes 112 emit the group of electrical currents 108 into medium 106 when the group of electrodes 112 are located in medium 106.

In one illustrative example, controller 116 identifies target location 134 in medium 106 using the group of parameters 132. In one illustrative example, controller 116 can determine a group of parameters 132 from electrical signals 136 in medium 106 detected using the group of electrodes 112. The electrical signals can include a voltage, a current, or both a voltage and a current. For example, target locations include one or more neurons. Neurons can be identified based on electrical activity. Some additional nonlimiting examples of target locations include a medulla oblongata, an atrium in a heart, a ventricle in the heart, a spinal nerve, and other suitable structures that can be subjected to an electrical current to obtain a desired effect.

Controller 116 selects a group of characteristics 128 for the group of electrical currents 108 such that the group of electrical currents 108 reaches the target location 134 when the group of electrical currents 108 is emitted from the group of electrodes 112 in medium 106. The group of characteristics 128 for the group of electrical currents 104 can include at least one of an amplitude for the group of electrical currents, a direction of the electrical current flow, an origination and termination for the electrical current, or other suitable characteristics. These characteristics can be used to generate a group of electrical currents that have a desired shape. Target location 134 can take a number of different forms. For example, target location 134 can be a location identified by a coordinate, a sphere, an irregular volume, a structure, or some other type of volume.

Controller 116 can be implemented in software, hardware, firmware or a combination thereof. When software is used, the operations performed by controller 116 can be implemented in program code configured to run on hardware, such as a processor unit. When firmware is used, the operations performed by controller can be implemented in program code and data and stored in persistent memory to run on a processor unit. When hardware is employed, the hardware can include circuits that operate to perform the operations in controller 116.

In the illustrative examples, the hardware can take a form selected from at least one of a circuit system, an integrated circuit, an application specific integrated circuit (ASIC), a programmable logic device, or some other suitable type of hardware configured to perform a number of operations. With a programmable logic device, the device can be configured to perform the number of operations. The device can be reconfigured at a later time or can be permanently configured to perform the number of operations. Programmable logic devices include, for example, a programmable logic array, a programmable array logic, a field programmable logic array, a field programmable gate array, and other suitable hardware devices. Additionally, the processes can be implemented in organic components integrated with inorganic components and can be comprised entirely of organic components excluding a human being. For example, the processes can be implemented as circuits in organic semiconductors.

Computer system 117 is a physical hardware system and includes one or more data processing systems. When more than one data processing system is present in computer system 117, those data processing systems are in communication with each other using a communications medium. The communications medium can be a network. The data processing systems can be selected from at least one of a computer, a server computer, a tablet computer, or some other suitable data processing system.

In this illustrative example, electrical stimulation system 102 can also deliver substance 140 through delivery tubes 142 into medium 106 when a group of ends of delivery tubes 142 are located in medium 106.

Substance 140 can be at least one of a fluid, a nutrient, a medicine, or other type of substance. In this illustrative example, the delivery of substance 140 is controlled by controller 116.

In one illustrative example, electrodes 112, optical fibers 114, and delivery tubes 142 can be integrated into structures such as probes. For example, an electrode in electrodes 112, an optical fiber in optical fibers 114, and a delivery tube in delivery tubes 142 can be integrated into a component such as a probe. With this depicted example, the electrode can be in the form of a tubular structure that provides a housing in the probe for the optical fiber and the delivery tube.

In one illustrative example, one or more technical solutions are present that overcome a technical problem with sending electrical currents into the medium with a desired level of feedback. As a result, one or more technical solutions can provide a technical effect receiving sensor data from optical fibers located in the medium when the electrodes. In one illustrative example, the optical fibers are integrated with electrodes in the probe located in the medium. In the illustrative example, one or more technical solutions enable sending electrical current with a level of precision that cause the current to flow through a target location and in a manner that reduces the flow of electrical current into other areas for which electrical current is not desired or needed.

Further, in another illustrative example, delivery tubes are present that enable the delivery of substances into the medium. The substances can be used to cause changes in the medium. The substances can be used after delivery or in conjunction with the delivery of electrical currents.

Figure 2:
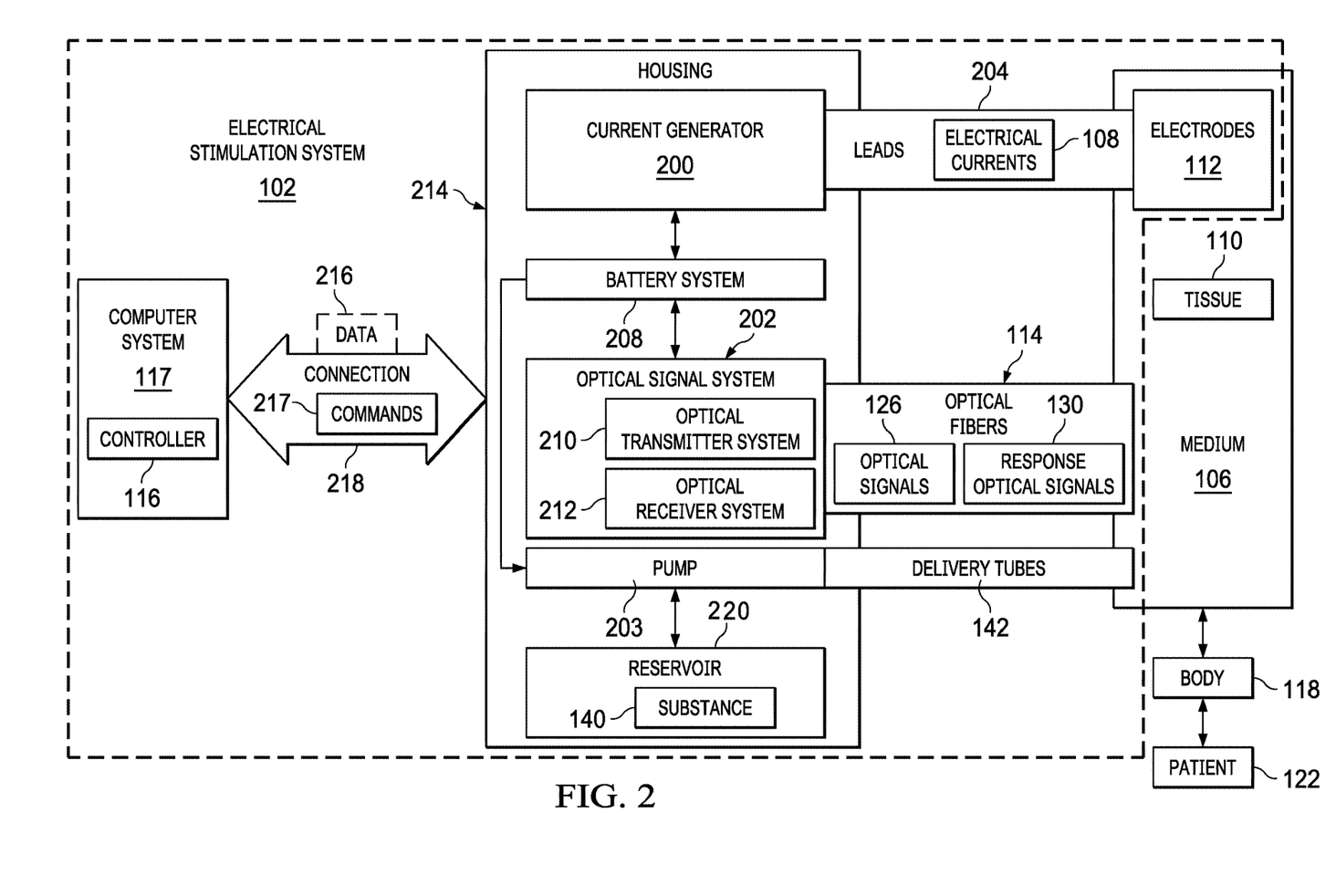
FIG. 2 is a more detailed illustration of a block diagram of an electrical stimulation system in accordance with an illustrative example.

With reference now to FIG. 2, a more detailed illustration of a block diagram of an electrical stimulation system is depicted in accordance with an illustrative example. In the illustrative examples, the same reference numeral may be used in more than one figure. This reuse of a reference numeral in different figures represents the same element in the different figures.

In this more detailed example, electrical stimulation system 102 includes controller 116, a group of electrodes 112, a group of optical fibers 114, a group of delivery tubes 142, current generator 200, optical signal system 202, pump 203, and a group of leads 204.

In this illustrative example, current generator 200 is connected to the group of electrodes 112 by the group of leads 204. The group of leads 204 is a group of cables that can be implanted in medium 106. The group of leads 204 is insulated while the group of electrodes 112 is uninsulated.

In this illustrative example, current generator 200 is designed to be placed in medium 106. As depicted, current generator 200 can be, for example, a neurostimulator, a cardiac pacemaker, or some other type of current source. Current generator 200 can operate using power from battery system 208 to generate the electrical currents 108.

Further, when current generator 200 is implanted in medium 106 such as body 118, battery system 208 can be rechargeable without removing the battery or using a physical connection. For example, wireless power transfer techniques such as inductive charging can be used.

In this illustrative example, optical signal system 202 is a hardware system and is connected to the group of optical fibers 114. Optical signal system 202 can also operate using power from battery system 208.

As depicted, optical signal system 202 includes optical transmitter system 210 and optical receiver system 212. Optical transmitter system and optical signal system 202 can be comprised of one or more optical transmitters. An optical transmitter can be, for example, a semiconductor device such as light-emitting diodes (LED) or laser diodes. The optical transmitter system operates to send optical signals 126 through the group of optical fibers 114.

As depicted, optical receiver system in optical signal system 202 is connected to the group of optical fibers 114. This connection is also an optical connection. The optical receiver system can be one or more optical receivers. An optical receiver can be a photodetector that converts light into electricity using the photoelectric effect. The optical receiver system operates to detect response optical signals 130 occurring in response to optical signals 126 being sent into the group of optical fibers 114 by the optical transmitter system 210. These two systems can be implemented as an optical transceiver system in which the same system transmits optical signals 126 and receives response optical signals 130.

In this illustrative example, current generator 200 and optical signal system 202 are located in housing 214. In this illustrative example, housing 214 can be implantable in medium 106 or can be located outside of medium 106.

Controller 116 controls the operation of current generator 200, optical signal system 202, and pump 203. As depicted, controller 116 can be located in computer system 117. In some illustrative examples, controller 116 can be located in housing 214 depending on the particular implementation.

Controller 116 sends commands 217 through connection 218 to current generator 200, optical signal system 202, and pump 203. Commands 217 are used to control the operation these components. Connection 218 can be established using at least one of a wired communications link, an optical communications link, or a wireless communications link.

In this illustrative example, optical signal system 202 sends data 216 to controller 116 through connection 218.

Data 216 can be sensor data, settings, or other information from optical signal system 202. In some illustrative examples, current generator 200 also sends data 216 to controller 116. For example, current generator 200 send current settings. Additionally, current generator 200 can also send sensor data such as voltages detected between electrodes 112 or electrical currents 108 flowing between electrodes 112 or between segments 138 and electrodes 112.

In the illustrative example, pump 203 and delivery tubes 142 provide a mechanism to deliver substance 140 into medium 106. As depicted, substance 140 is stored in reservoir 220. Pump 203 can move substance 140 from reservoir 220 through the group of delivery tubes 142 into medium 106. Although reservoir 220 is used to store substance 140 in this example, substance 140 can be stored in other ways such as within the group of delivery tubes 142 other illustrative examples.

Figure 3:
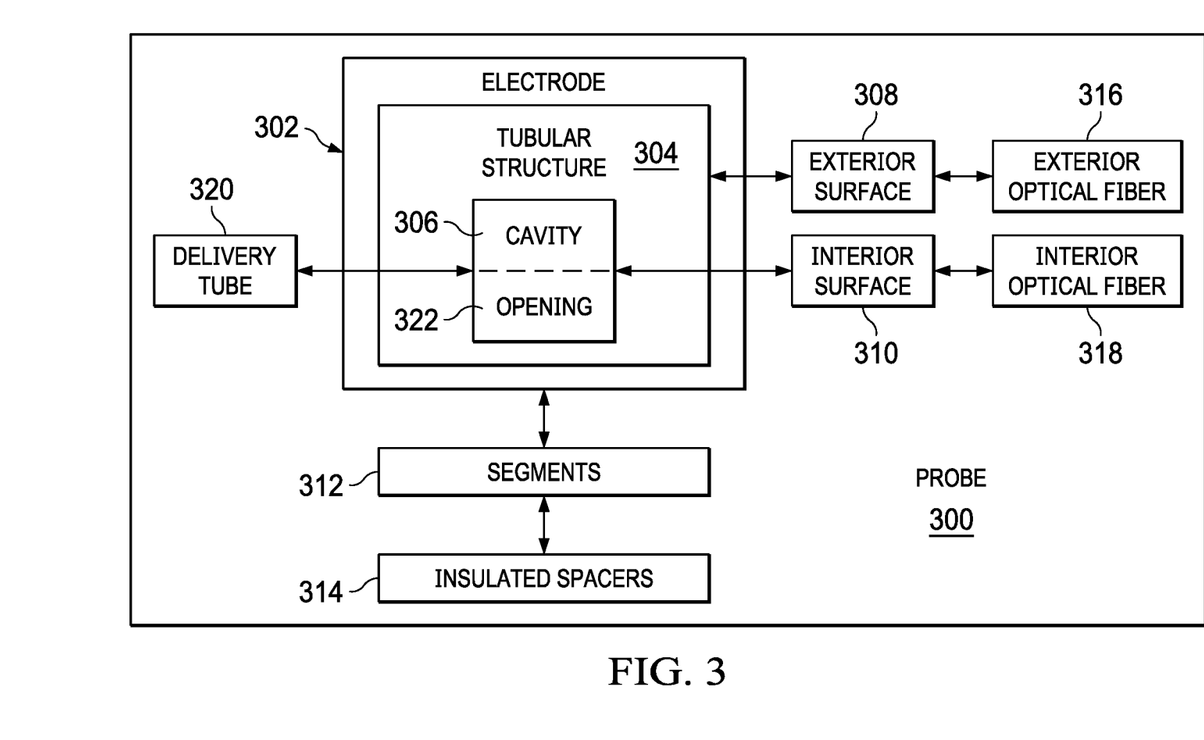
FIG. 3 is an illustration of a block diagram of a probe in accordance with an illustrative example.

Turning next to FIG. 3, an illustration of a block diagram of a probe is depicted in accordance with an illustrative example. In this illustrative example, probe 300 can integrate components such the group of electrodes 112 and the group of optical fibers 114.

In one illustrative example, electrode 302 in the group of electrodes 112 provides a structure for probe 300. As depicted, electrode 302 has tubular structure 304. In this example, tubular structure 304 for probe 300 has cavity 306. Tubular structure 304 has exterior surface 308 and interior surface 310 in cavity 306.

As depicted, electrode 302 is segmented. In other words, segments 312 are conductive portions of electrode 302 that are separated by insulated spacers 314.

In this illustrative example, exterior optical fiber 316 is connected the exterior surface 308 for tubular structure 304 of electrode 302 in probe 300.

In this illustrative example, delivery tube 320 in group of delivery tubes 142 can also be part of probe 300. As depicted, delivery tube 320 extends through cavity 306 within tubular structure 304. Cavity 306 has opening 322 through which substance 140 can be delivered into a tissue though delivery tube 320.

In this manner, probe 300 provides an integrated electrical current delivery and sensor system. With the sensor system located proximately to the current delivery mechanism, a more accurate determination of the conditions of the medium can be determined as per using other sensors located farther away. Further, delivery tube 320 can provide additional options for causing desired effects in a medium such as tissue are present within ability to deliver substances such as fluids, medications, or other types of substances suitable for use in a particular type of medium.

The illustration of electrical stimulation environment 100 and the different components in electrical stimulation environment 100 in FIGS. 1-3 is not meant to imply physical or architectural limitations to the manner in which an illustrative example may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative example.

For example, controller 116 can be implemented in housing 214 in some illustrative examples. In another example, delivery tube 320 can be located on the exterior surface 308 of tubular structure 304 instead of being located within cavity 306. In other illustrative examples, one delivery tube in addition to delivery tube 320 can be present in cavity 306 or on exterior surface 308 of tubular structure 304. In still other examples, at least one of exterior optical fiber 316, interior optical fiber 318, or delivery to 320 can be implemented separately from probe 300 instead of being part of probe 300.

As another example, controller 116 in FIG. 1 is shown as a single functional component. In some illustrative examples, controller 116 can be distributed. For example, controller 116 can be located in computer system 117 and in housing 214.

Figure 4:
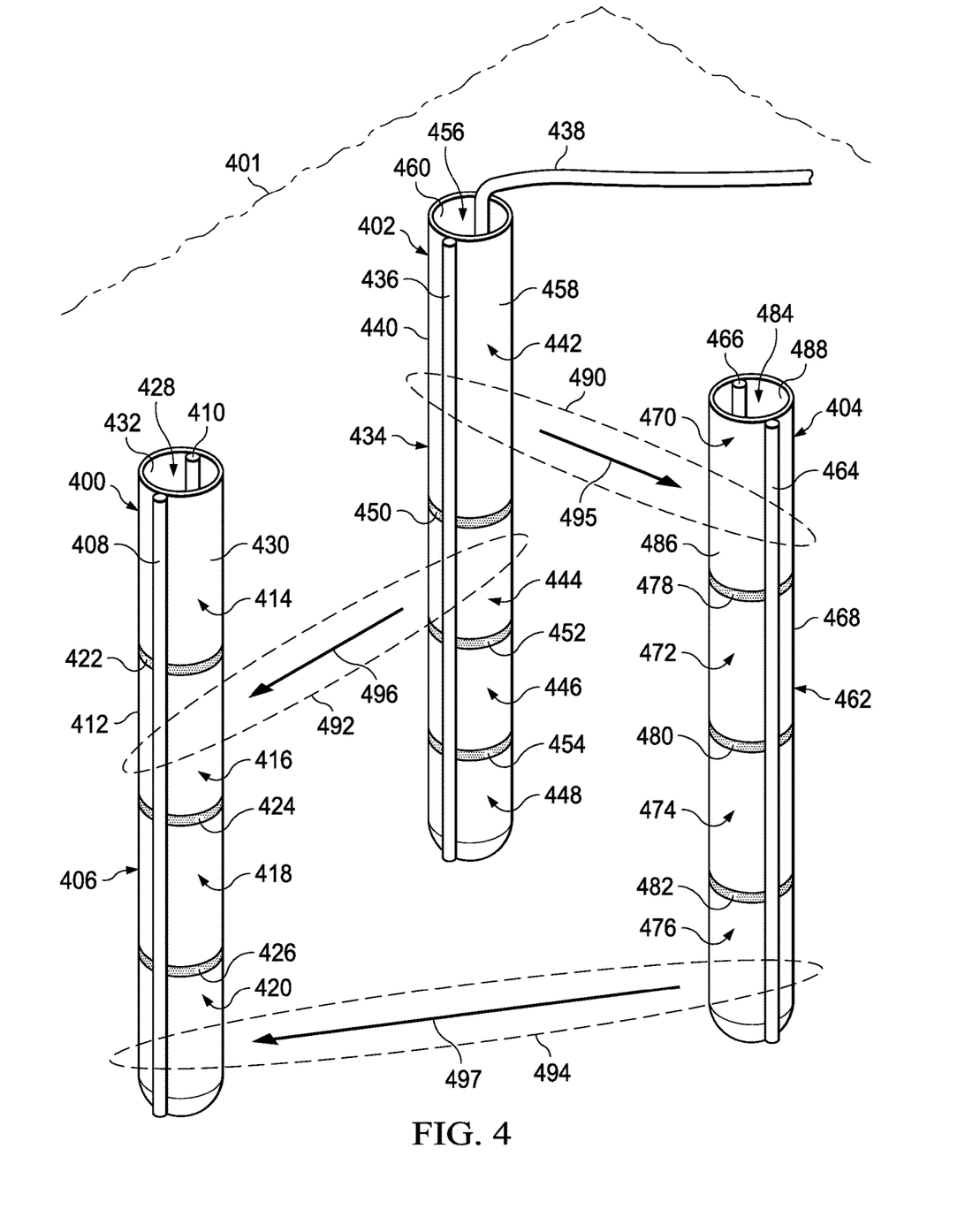
FIG. 4 is an illustration of a group of probes in accordance with an illustrative example.

With reference next to FIG. 4, an illustration of a group of probes is depicted in accordance with an illustrative example. In this example, probe 400, probe 402, and probe 404 are examples of implementations for probe 300 shown in block form in FIG. 3.

As depicted, probe 400 is comprised of electrode 406, exterior optical fiber 408, and interior optical fiber 410. In this example, electrode 406 is in the form of tubular structure 412, which is segmented.

In this illustrative example, segment 414, segment 416, segment 418, and segment 420 form electrode 406. These segments are conductive cylinders separated from each other by insulated spacers. As depicted, insulated spacer 422 separates segment 414 and segment 416. Insulated spacer 424 separates segment 416 and segment 418, and insulated spacer 426 separates segment 418 and segment 420.

As depicted, cavity 428 is present in tubular structure 440 of electrode 406. Exterior optical fiber 408 is located on exterior surface 430 of electrode 406. Interior optical fiber 410 is located on interior surface 432 of electrode 406 in cavity 428.

In the illustrative example, probe 402 is comprised of electrode 434, exterior optical fiber 436, and interior optical fiber 438. In this example, electrode 434 has the form of tubular structure 440, which is segmented.

In this illustrative example, electrode 434 is comprised of segment 442, segment 444, segment 446, and segment 448. These segments are conductive cylinders separated from each other by insulated spacers. As depicted, insulated spacer 450 separates segment 442 and segment 444, and insulated spacer 452 separates segment 444 and segment 446. Insulated spacer 454 separates segment 446 and segment 448.

As depicted, electrode 434 has cavity 456 extending through tubular structure 440 for electrode 434. Exterior optical fiber 436 is located on exterior surface 458 of electrode 434. Interior optical fiber 438 is located on interior surface 460 in cavity 456.

As depicted, probe 404 is comprised of electrode 462, exterior optical fiber 464, and interior optical fiber 466. In this example, electrode 462 is in the form of tubular structure 468, which is segmented.

In this illustrative example, segment 470, segment 472, segment 474, and segment 476 form electrode 462. In this illustrative example, these segments are in the form of conductive cylinders that can be stacked or lined up in arrays to form the probes. The conductive cylinders are electrically separated from each other in a probe by insulated spacers. This separation enables selecting one segment to conduct an electrical current in a manner that the electrical current does not also flow into an adjacent segment. This separation can enable more control over the electrical current.

As depicted, insulated spacer 478 separates segment 470 and segment 472. Insulated spacer 480 separates segment 472 and segment 474. Insulated spacer 482 separates segment 474 and segment 476.

Cavity 484 is located in tubular structure 468 for electrode 462. Exterior optical fiber 464 is located on exterior surface 486 of electrode 462. Interior optical fiber 466 is located on interior surface 488 in cavity 484.

As depicted, these electrodes are located in tissue 401 and can be operated by a controller to cause current flow between the different segments in the electrodes. In this illustrative example, current flow 490 is from segment 442 in electrode 434 to segment 470 in electrode 462 in the direction of arrow 495. The polarities of these segments are set by the desired direction of current flow. As depicted, segment 442 is positive while segment 470 is negative.

As another example, current flow 492 flows from segment 444 in electrode 434 to segment 416 in electrode 406 in the direction of arrow 496. In this illustrative example, segment 444 is positive while segment 416 is negative.

This figure also includes current flow 494 from segment 476 in electrode 462 to segment 420 in electrode 406 in the direction of arrow 497. In this illustrative example, segment 476 is positive while segment 420 is negative.

In this illustrative example, the optical fibers can be used to detect information about tissue 401. For example, the information can include at least one of a temperature, a blood pressure, or other parameters. This information can be for the tissue through which electrical current is flowing based on the information from portions of the optical fibers. The information can also be for the condition for which the electrical currents are being emitted. This information can be used as feedback to adjust the characteristics of electrical currents. With the information being detected for tissue 401 affected by the current flow, feedback can be provided for making adjustments to the current flow generated by at least one of probe 400, probe 402, or probe 404. The flow of electrical current between these probes can be selected such that the electrical currents reach desired areas or structures in tissue 401. In the illustrative example, a switching system can be implemented that is controlled by at least one of a controller or a current generator. This switching system can include a switch in an integrated circuit that is connected to a current generator and connects to segments in the probe. The switch can be operated to select which segments in a probe to conduct current. The commands to control the switches can be sent through wireless signals or cables connecting the electrodes.

Figure 5:
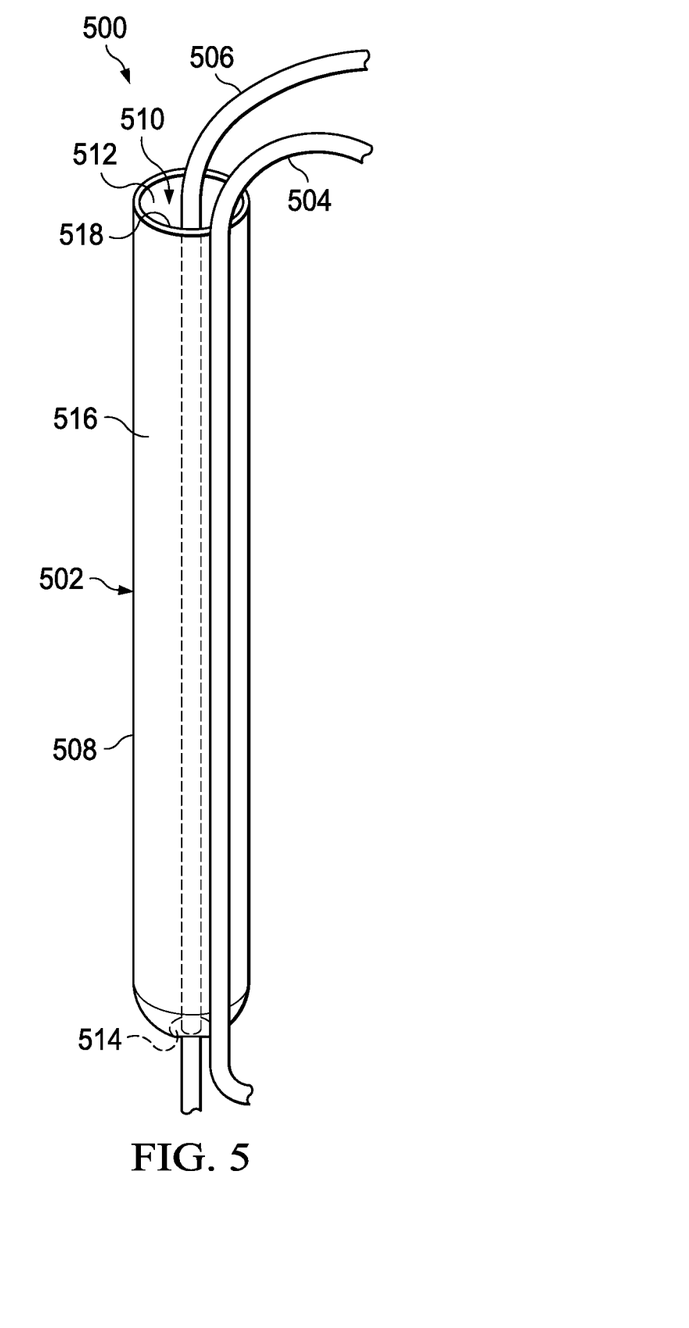
FIG. 5 is an illustration of a probe in accordance with an illustrative example.

With reference next to FIG. 5, an illustration of a probe is depicted in accordance with an illustrative example. In this figure, probe 500 is comprised of electrode 502, optical fiber 504, and delivery tube 506.

Electrode 502 is in the form of tubular structure 508 with cavity 510 extending through tubular structure 508. In this depicted example, tubular structure 508 includes opening 512 and opening 514. Cavity 510 is in communication with these two openings in tubular structure 508.

In this depicted example, optical fiber is on exterior surface 516 of tubular structure 508 for electrode 502. Delivery tube 506 is located on interior surface 518 in cavity 510 in tubular structure 508 for electrode 502.

The illustration of the probes in FIG. 4 and FIG. 5 are provided as illustrative nonlimiting examples of how probe 300 shown in block form in FIG. 3 can be implemented. These illustrations are not meant to limit the manner in which other examples can be implemented. For example, some other number of probes can be used in other examples of referrals shown in FIG. 4. For example, one probe, 5 probes, 10 probes, or some other number of probes can be used. Further, some probes can be segmented while other probes are not segmented. As another example, delivery tube 506 can be located in cavity 510 in tubular structure 508 without being connected to interior surface 518.

As another example, the segments can have forms other than a cylinder. For example, the segments can have other cross-sectional shapes selected from at least one of a rectangle, a square, a pentagon, a hexagon, an irregular shape, or some other suitable shape. Further, the different segments in the probe can taper in size.

Figure 6:
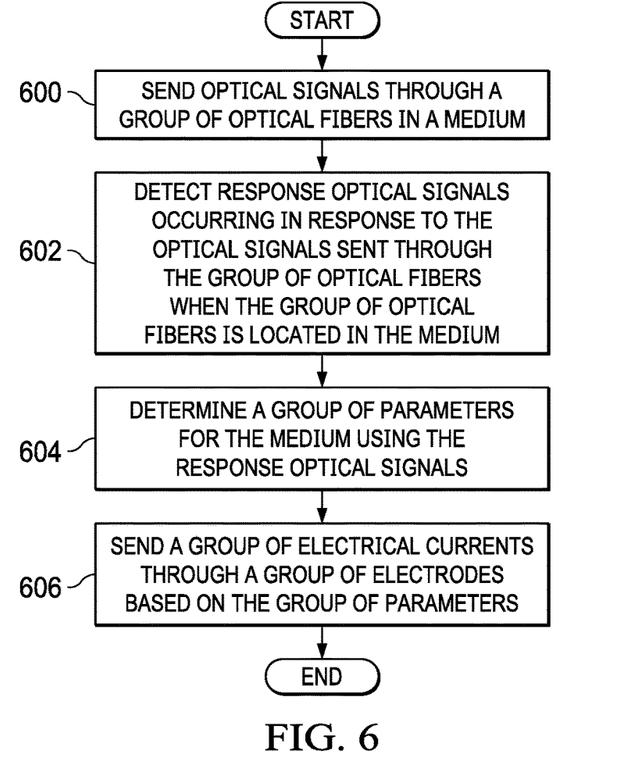
FIG. 6 is an illustration of a flowchart of a process for delivering electrical current in accordance with an illustrative example.

Turning next to FIG. 6, an illustration of a flowchart of a process for delivering electrical current is depicted in accordance with an illustrative example. The process in FIG. 6 can be implemented in hardware, software, or both. When implemented in software, the process can take the form of program code that is run by one or more processor units located in one or more hardware devices in one or more computer systems. For example, the process can be implemented in a component such as controller 116 in computer system 117 in FIG. 1. This process can be used to control different components in electrical stimulation system 102 in FIG. 1.

The process begins by sending optical signals through a group of optical fibers in a medium (operation 600). The process detects response optical signals occurring in response to the optical signals sent through the group of optical fibers when the group of optical fibers is located in the medium (operation 602).

The process determines a group of parameters for the medium using the response optical signals (operation 604). The process sends a group of electrical currents through a group of electrodes based on the group of parameters (operation 606). The process terminates thereafter. The group of electrodes emit the group of electrical currents sent in operation 606. In this illustrative example, the electrical current flow for each current is from one electrode to another electrode. In flowing from one electrode to another electrode, the electrical current flow may be from a first segment in a first electrode to a second segment in a second electrode. As another example, the electrical current flow can be from the first segment in the first electrode to many segments in the second electrode or from many segments in the first electrode to many segments of the second electrode, or other combinations of electric current flow.

Figure 7:
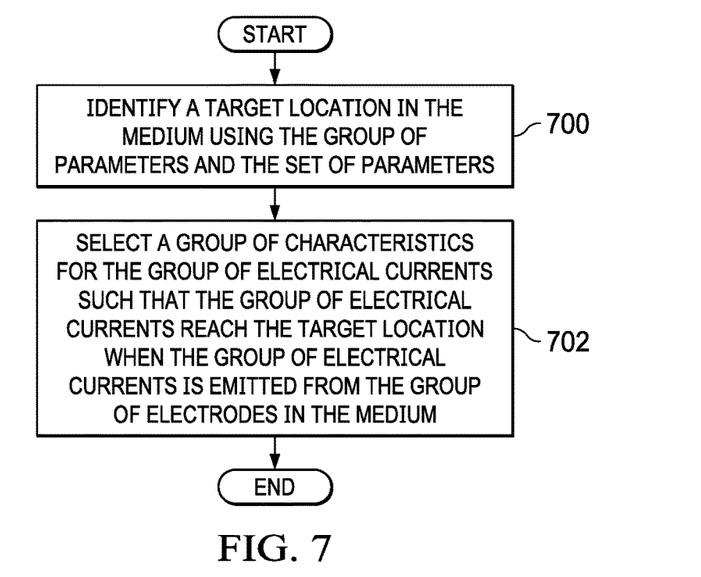
FIG. 7 is an illustration of a flowchart of a process for selecting characteristics for a group of electrical currents in accordance with an illustrative example.

With reference next to FIG. 7, an illustration of a flowchart of a process for selecting characteristics for a group of electrical currents is depicted in accordance with an illustrative example. The process illustrated in this figure can be used to select the group of parameters in operation 606 in FIG. 6.

The process begins by identifying a target location in a medium using a group of parameters for the medium (operation 700). In this example, the medium can be tissue such as brain tissue in brain of a patient. The target can be one or more neurons. The location of the one or more neurons is the target location. The neurons can be identified based on electrical activity or other parameters. The target can be neurons with electrical activity or parameters that indicate abnormal passing of messages from neuron to neuron across a synapse such as dopamine.

The process selects a group of characteristics for the group of electrical currents such that the group of electrical currents reach the target location when the group of electrical currents is emitted from the group of electrodes in the medium (operation 702). The process terminates thereafter.

In operation 702, the group of electrical currents have a group of characteristics such that the group of electrical currents is emitted from the group of electrodes with a desired shape.

As depicted, characteristics for the group of electrical currents can include at least one of an amplitude for the group of electrical currents, a direction of the electrical current flow, and an origination and termination for the electrical current, or other suitable characteristics. These characteristics can be used to generate a group of electrical currents that have a desired shape.

For example, the amplitude for the group of electrical currents can be set such that each electrical current can have same amplitude or different electrical currents can have different amplitudes. Further, the electrodes used in the electrical current flow to generate a volume through which electrical current flow occurs can be selected such that the volume has a shape encompasses target.

The shape of the electrical current can be selected based on controlling the current flow between electrodes. For example, switchable polarities in the between segments can be used to change the direction of current flow as well as used to select how current flows between segments in electrodes.

For example, with electrical current flow from one electrode to another electrode, the electrical current flow may be from a first segment in a first electrode to a second segment in a second electrode. As another example, when the electrodes are comprised of segments, the group of electrical currents can flow from at least one of the segments in electrodes to another segment in the group of electrodes.

For example, the electrical current flow can be from the first segment in the first electrode to many segments in the second electrode or from many segments in the first electrode to many segments of the second electric. In yet another example, the electrical current flow can be from a first segment in an electrode to a second segment in the electrode.

By selecting which electrodes in which segments are used for electrical current flow, a desired shape can be generated for the electrical current flow of the group of electrical currents that encompasses the target.

Figure 8:
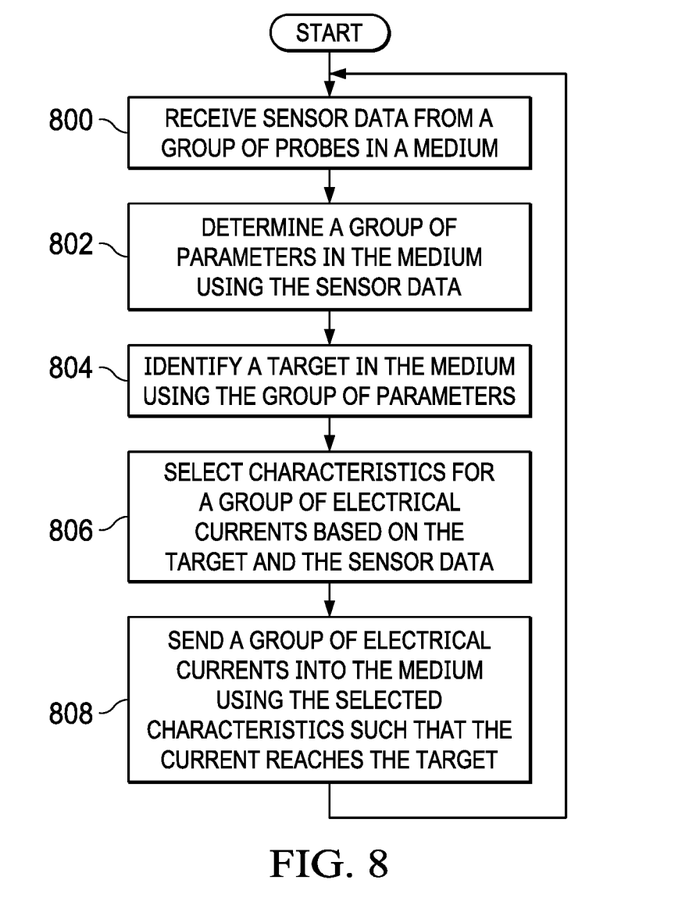
FIG. 8 is an illustration of a flowchart of a process for delivering an electrical current in the medium in accordance with an illustrative example.

With reference next to FIG. 8, a flowchart of a process for delivering an electrical current in the medium is depicted in accordance with an illustrative example. The process in FIG. 8 can be implemented in hardware, software, or both. When implemented in software, the process can take the form of program code that is run by one or more processor units located in one or more hardware devices in one or more computer systems. For example, the process can be implemented in a component such as controller 116 in computer system 117 in FIG. 1. This process can be used to control different components in electrical stimulation system 102 in FIG. 1.

The process begins by receiving sensor data from a group of probes in a medium (operation 800). The sensor data can be generated using at least one of optical fibers or electrodes in the group of probes. The sensor data can include response optical signals generated in response to the optical signals sent through the optical fibers. The sensor data can also include a voltage difference or current detected between at least one of electrodes or segments in the probes. The process determines a group of parameters in the medium using the sensor data (operation 802).

The process identifies a target in the medium using the group of parameters (operation 804). The process selects characteristics for a group of electrical currents based on the target and the sensor data (operation 806). In this illustrative example, the characteristics may include the amplitude or power to be delivered into the medium. Additionally, the characteristics also may be used to select a shape for the current flow through medium.

In operation 806, the target can be a same target as previously identified. If the target does not change, the characteristics can be changed based on changes detected for the target. In another illustrative example, identifying a target involves identifying a new target.

The process sends the group of electrical currents into the medium using the selected characteristics such that the current reaches the target (operation 808). The process returns to operation 800.

The flowcharts and block diagrams in the different depicted examples illustrate the architecture, functionality, and operation of some possible implementations of apparatuses and methods in an illustrative example. In this regard, each block in the flowcharts or block diagrams can represent at least one of a module, a segment, a function, or a portion of an operation or step. For example, one or more of the blocks can be implemented as program code, hardware, or a combination of the program code and hardware. When implemented in hardware, the hardware can, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams can be implemented using special purpose hardware systems that perform the different operations or combinations of special purpose hardware and program code run by the special purpose hardware.

In some alternative implementations of an illustrative example, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Figure 9:
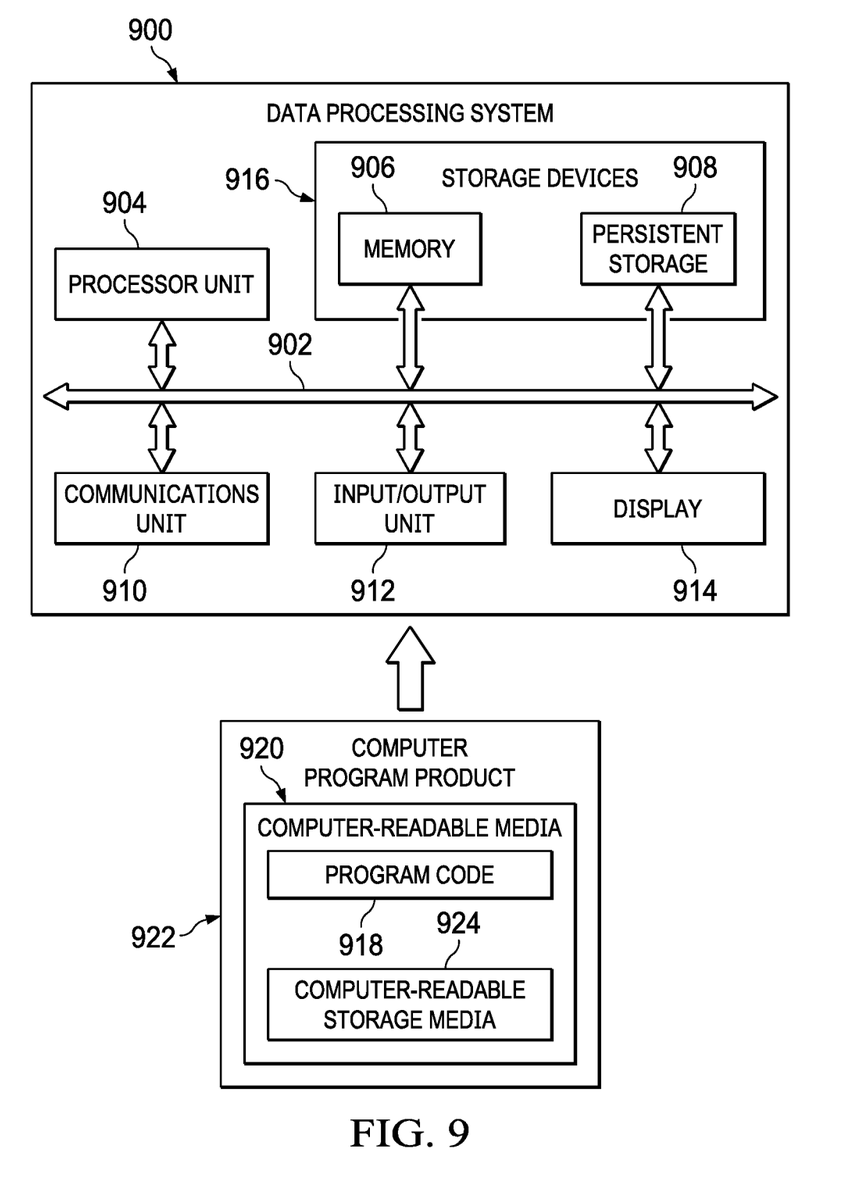
FIG. 9 is an illustration of a block diagram of a data processing system in accordance with an illustrative example.

Turning now to FIG. 9, an illustration of a block diagram of a data processing system is depicted in accordance with an illustrative example. Data processing system 900 can be used to implement one or more data processing systems in computer system 117 in FIG. 1. In this illustrative example, data processing system 900 includes communications framework 902, which provides communications between processor unit 904, memory 906, persistent storage 908, communications unit 910, input/output (I/O) unit 912, and display 914. In this example, communications framework 902 takes the form of a bus system.

Processor unit 904 serves to execute instructions for software that can be loaded into memory 906. Processor unit 904 includes one or more processors. For example, processor unit 904 can be selected from at least one of a multicore processor, a central processing unit (CPU), a graphics processing unit (GPU), a physics processing unit (PPU), a digital signal processor (DSP), a network processor, or some other suitable type of processor.

Memory 906 and persistent storage 908 are examples of storage devices 916. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 916 may also be referred to as computer-readable storage devices in these illustrative examples. Memory 906, in these examples, can be, for example, a random-access memory or any other suitable volatile or non-volatile storage device. Persistent storage 908 can take various forms, depending on the particular implementation.

For example, persistent storage 908 may contain one or more components or devices. For example, persistent storage 908 can be a hard drive, a solid-state drive (SSD), a flash memory, a rewritable optical disk, a rewritable magnetic tape, or some combination of the above. The media used by persistent storage 908 also can be removable. For example, a removable hard drive can be used for persistent storage 908.

Communications unit 910, in these illustrative examples, provides for communications with other data processing systems or devices. In these illustrative examples, communications unit 910 is a network interface card.

Input/output unit 912 allows for input and output of data with other devices that can be connected to data processing system 900. For example, input/output unit 912 can provide a connection for user input through at least one of a keyboard, a mouse, or some other suitable input device. Further, input/output unit 912 can send output to a printer. Display 914 provides a mechanism to display information to a user.

Instructions for at least one of the operating system, applications, or programs can be located in storage devices 916, which are in communication with processor unit 904 through communications framework 902. The processes of the different examples can be performed by processor unit 904 using computer-implemented instructions, which can be located in a memory, such as memory 906.

These instructions are referred to as program code, computer usable program code, or computer-readable program code that can be read and executed by a processor in processor unit 904. The program code in the different examples can be embodied on different physical or computer-readable storage media, such as memory 906 or persistent storage 908.

Program code 918 is located in a functional form on computer-readable media 920 that is selectively removable and can be loaded onto or transferred to data processing system 900 for execution by processor unit 904. Program code 918 and computer-readable media 920 form computer program product 922 in these illustrative examples. In the illustrative example, computer-readable media 920 is computer-readable storage media 924.

In these illustrative examples, computer-readable storage media 924 is a physical or tangible storage device used to store program code 918 rather than a medium that propagates or transmits program code 918.

Alternatively, program code 918 can be transferred to data processing system 900 using a computer-readable signal media. The computer-readable signal media can be, for example, a propagated data signal containing program code 918. For example, the computer-readable signal media can be at least one of an electromagnetic signal, an optical signal, or any other suitable type of signal. These signals can be transmitted over connections, such as wireless connections, optical fiber cable, coaxial cable, a wire, or any other suitable type of connection.

The different components illustrated for data processing system 900 are not meant to provide architectural limitations to the manner in which different examples can be implemented. In some illustrative examples, one or more of the components may be incorporated in or otherwise form a portion of, another component. For example, memory 906, or portions thereof, can be incorporated in processor unit 904 in some illustrative examples. The different illustrative examples can be implemented in a data processing system including components in addition to or in place of those illustrated for data processing system 900. Other components shown in FIG. 9 can be varied from the illustrative examples shown. The different examples can be implemented using any hardware device or system capable of running program code 918.

Thus, the illustrative examples provide a method, an apparatus, and a system for delivering an electrical current to a medium. In one illustrative example, optical signals are sent through a group of optical fibers in a medium. Response optical signals occurring in response to the optical signals sent through the group of optical fibers are detected when the group of optical fibers is located in the medium. A group of parameters are determined for the medium using the response optical signals. A group of electrical currents is sent through a group of electrodes based on the group of parameters, wherein the group of electrodes emit the group of electrical currents. These parameters can be used to select a group of characteristics for the group of electrical currents.

Further, polarities can be configured for segments in electrodes enabling increased fine tuning of the administered electrical field generated by current flow of the group of the electrical currents. This selectivity can be important with the specifically localized regions of the brain that are generally responsible for tremor activities. By more tightly controlling the shape current flow, specific areas of the brain associated with these conditions can be more effectively treated, reducing unnecessary potential effects on neighboring tissues not requiring stimulation.

Further, the ability to shape the current flow can reduce overall current needs to produce effective fields, resulting in less power consumption and longer power stores as well as reduced opportunity for over stimulation over time of the affected area. Further, the illustrative examples can be used for diagnostic purposes in addition to or in place of treatment of conditions.

The description of the different illustrative examples has been presented for purposes of illustration and description and is not intended to be exhaustive or limited to the examples in the form disclosed. The different illustrative examples describe components that perform actions or operations. In an illustrative example, a component can be configured to perform the action or operation described. For example, the component can have a configuration or design for a structure that provides the component an ability to perform the action or operation that is described in the illustrative examples as being performed by the component.

Many modifications and variations will be apparent to those of ordinary skill in the art. Further, different illustrative examples may provide different features as compared to other desirable examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. An electrical stimulation system comprising:
   a number of electrodes, wherein each electrode has a tubular structure having an external surface and an internal surface in a cavity in the tubular structure, and wherein the tubular structure comprises a number of segments;
   a first optical fiber located on the external surface;
   a second optical fiber located on the internal surface;
   a controller that controls operation of the electrodes and the optical fibers, wherein the controller sends optical signals through the optical fibers; detects response optical signals occurring in response to the optical signals sent through the optical fibers when the optical fibers are located in a medium; determines one or more parameters for the medium using the response optical signals; and sends one or more electrical currents through the electrodes based on the parameters, wherein the electrodes emit the electrical currents between each other through the medium when the electrodes are located in the medium such that a current loop pathway is shaped as the electrical currents traverse the medium; and
   a switch controlled by the controller, wherein the switch is configured to switch polarities of the segments of the electrodes to change current flow between the electrodes and between segments of the same electrode.

2. The electrical stimulation system of claim 1, wherein the controller identifies a target location in the medium using the parameters and selects one or more characteristics for the electrical currents such that the electrical currents reach the target location when the electrical currents are emitted from the electrodes in the medium.

3. The electrical stimulation system of claim 2, wherein the characteristics comprise at least one of an amplitude, a voltage, an electrode current flow, a direct current flow, an alternating current flow, or a pattern in current flow.

4. The electrical stimulation system of claim 1, wherein the controller determines the parameters from electrical signals detected using the electrodes.

5. The electrical stimulation system of claim 4, wherein the controller identifies a target location in the medium using the parameters and selects one or more characteristics for the electrical currents such that the electrical currents reach the target location when the electrical currents are emitted from the electrodes in the medium.

6. The electrical stimulation system of claim 1, wherein the electrical currents have characteristics such that the electrical currents emitted from the electrodes flow between the electrodes with a desired shape.

7. The electrical stimulation system of claim 1 further comprising:
   one or more delivery tubes, wherein the controller sends at least one of a fluid, a nutrient, or a medicine through the delivery tubes into the medium at one or more ends of the delivery tubes located in the medium.

8. The electrical stimulation system of claim 7, wherein the delivery tubes are located on at least one of the external surface or the internal surface.

9. An electrical stimulation system comprising:
   electrodes having tubular structures with exterior surfaces and interior surfaces in cavities in the electrodes, wherein the tubular structure comprises a number of segments;
   optical fibers configured to be placed into an interior of a system, wherein the optical fibers are located on at least one of the exterior surfaces or the interior surfaces;
   a controller that sends optical signals through the optical fibers, detects response optical signals occurring in response to the optical signals sent through optical fibers when the optical fibers are located in a medium, determines one or more parameters for the medium using the response optical signals, and sends one or more electrical currents through the electrodes based on the parameters, wherein the electrodes emit the electrical currents between each other through the medium when the electrodes are located in the medium such that a current loop pathway can be shaped as the electrical currents traverse the medium; and
   a switch controlled by the controller, wherein the switch is configured to switch polarities of the segments of the electrodes to change current flow between the electrodes and between segments of the same electrode.

10. The electrical stimulation system of claim 9 further comprising:
    an optical transceiver connected to the optical fibers, wherein the controller controls the optical transceiver to send the optical signals through the optical fibers and detects response optical signals occurring in response to the optical signals sent through optical fibers when the optical fibers are located in the medium; and
    a current generator connected to the electrodes, wherein the controller controls the current generator to send the electrical currents through the electrodes based on the parameters, wherein the electrodes emit the electrical currents into the medium when electrodes are located in the medium.

11. The electrical stimulation system of claim 9, wherein controller identifies a target location in the medium using the parameters and selects one or more characteristics for the electrical currents such that the electrical currents reach the target location when the electrical currents is emitted from the electrodes in the medium.

12. The electrical stimulation system of claim 9 further comprising:
    one or more delivery tubes, wherein the delivery tubes are located on at least one of the exterior surfaces or the interior surfaces and wherein the controller sends a fluid through the delivery tubes into the medium when one or more ends of the delivery tubes are located in the medium.

13. The electrical stimulation system of claim 12 further comprising:
    a pump connected to the delivery tubes and the controller, wherein the controller controls the pump, the pump configured to send the fluid through the delivery tubes into the medium when the ends of the delivery tubes are located in the medium.

14. A method for delivering an electrical current, the method comprising:
sending optical signals through one or more optical fibers in a medium;
detecting response optical signals occurring in response to the optical signals sent through the optical fibers when the optical fibers are located in the medium;
determining parameters for the medium using the response optical signals;
sending one or more electrical currents between a number of electrodes through the medium based on the parameters such that a current loop pathway can be shaped as the electrical currents traverse the medium, and wherein each electrode has a tubular structure comprising a number of segments having an external surface and an internal surface in a cavity in the tubular structure and wherein a first optical fiber is located on the external surface, and a second optical fiber is located on the internal surface; and
switch polarities of the segments of the electrodes to change current flow between the electrodes and between segments of the same electrode based on pre-determined trigger parameters.

15. The method of claim 14 further comprising:
identifying a target location in the medium using the parameters; and
selecting one or more characteristics for the electrical currents such that the electrical currents reach the target location when the electrical currents are emitted from the electrodes in the medium.

16. The method of claim 15, wherein the characteristics comprises at least one of an amplitude, a voltage, an electrode current, a direct current flow, an alternating current flow, or a pattern in current flow.

17. The method of claim 14, further comprising:
determining the parameters from electrical signals in the medium detected using the electrodes, wherein the electrical signals result from electrical activity of the medium.

18. The method of claim 17, further comprising:
identifying a target location in the medium using the parameters determined from the electrical signals; and
selecting one or more characteristics for the electrical currents such that the electrical currents reach the target location when the electrical currents are emitted from the electrodes in the medium.

19. The method of claim 14, wherein the electrical currents have one or more characteristics such that the electrical currents emitted from the electrodes flow between the electrodes with a desired shape.

20. The method of claim 14 further comprising:
sending at least one of a fluid, a nutrient, or a medicine through one or more delivery tubes into the medium at one or more ends of the delivery tubes located in the medium.

21. The method of claim 20, wherein the delivery tubes are located on at least one of the external surface or the internal surface.

22. The electrical stimulation system of claim 1, further comprising an optical signal system connected to the optical fibers, wherein the optical signal system comprises a light-emitting diode or laser diode.

23. The electrical stimulation system of claim 9, further comprising an optical signal system connected to the optical fibers, wherein the optical signal system comprises a light-emitting diode or laser diode.

24. The method of claim 14, wherein the medium comprises one of:
neurons; or
heart tissue.

25. The electrical stimulation system of claim 1, wherein polarities for segments of the same electrode can be set independently of each other.

26. The electrical stimulation system of claim 9, wherein polarities for segments of the same electrode can be set independently of each other.

27. The method of claim 14, wherein polarities for segments of the same electrode can be set independently of each other.

* * * * *